(12) United States Patent
Lundkvist

(10) Patent No.: US 9,347,861 B2
(45) Date of Patent: May 24, 2016

(54) FLUID SAMPLE HOLDERS WITH PISTON VALVE

(75) Inventor: Mats Lundkvist, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 7 days.

(21) Appl. No.: 14/234,437

(22) PCT Filed: Jul. 25, 2012

(86) PCT No.: PCT/EP2012/064610
§ 371 (c)(1),
(2), (4) Date: Jan. 23, 2014

(87) PCT Pub. No.: WO2013/014193
PCT Pub. Date: Jan. 31, 2013

(65) Prior Publication Data
US 2014/0174211 A1    Jun. 26, 2014

(30) Foreign Application Priority Data

Jul. 28, 2011  (GB) .................................. 1113009.3

(51) Int. Cl.
| G01N 1/00 | (2006.01) |
| G01N 1/28 | (2006.01) |
| B01L 3/02 | (2006.01) |
| G01N 35/10 | (2006.01) |
| B01L 3/00 | (2006.01) |

(52) U.S. Cl.
CPC ................ *G01N 1/28* (2013.01); *B01L 3/0217* (2013.01); *B01L 3/52* (2013.01); *G01N 35/1097* (2013.01); *B01L 3/502715* (2013.01); *B01L 2300/123* (2013.01); *B01L 2400/0478* (2013.01); *B01L 2400/0487* (2013.01); *B01L 2400/065* (2013.01)

(58) Field of Classification Search
None
See application file for complete search history.

(56) References Cited

U.S. PATENT DOCUMENTS 5,456,885 A    10/1995    Coleman et al.

FOREIGN PATENT DOCUMENTS

| FR | 2305713 | 10/1976 |
| WO | 93/22673 | 11/1993 |
| WO | 98/05426 | 2/1998 |

OTHER PUBLICATIONS

PCT/EP2012/064610 ISRWO dated Oct. 26, 2012.

*Primary Examiner* — Robert R Raevis
(74) *Attorney, Agent, or Firm* — Wood IP LLC

(57) ABSTRACT

Disclosed is a fluid sample holder 20 for delivering or receiving a fluid sample to or from fluid processing equipment such as a chromatography column 5 (FIG. 1). The sample holder 20 comprises: a sample fluid reservoir 15; a sample fluid port 23; a buffer fluid port 21; and a sliding seal 25 within the reservoir 15 having an external area 25S (FIG. 3) which generally sealing engages with a wall of the reservoir 15 thereby defining first 22 and second 24 fluid separated regions in the reservoir 15. The sliding seal 25 is displaceable within the reservoir 15 by means of a working fluid pressure differential between the first 22 and second 24 regions to thereby change the respective volumes of the first and second regions, and the external area at least is formed from a plastics molded material which elastically flexes when subjected to a pressure differential greater than the working fluid pressure differential and when so flexed allows fluid flow between the first and second regions.

11 Claims, 4 Drawing Sheets

FLUID SAMPLE HOLDERS WITH PISTON VALVE

This application is a filing under 35 U.S.C. 371 of international application number PCT/EP2012/064610, filed Jul. 25, 2012, which claims priority to Great Britain application number 1113009.3 filed Jul. 28, 2011, the entire disclosure of which is hereby incorporated by reference.

This invention relates to a sample holder, particularly, but not exclusively for allowing a fluid sample to be delivered to, or received from, a chromatography column or other fluid processing equipment.

Where small amounts of sample fluids need to be employed, for example in protein purification in a chromatographic process, in commercially available products, such sample fluids have been provided in fluid sample holders which have a reservoir connectable to a chromatography column. The reservoirs have an outlet for expelling the fluid and an inlet for accepting buffer fluid. In use the buffer fluid is pressurised to force the sample fluid out of the outlet. In order to separate the sample and buffer fluids, a moveable barrier between the sample fluid and the buffer fluid has been provided.

In the commercially available fluid sample holder this barrier is in the form of a sliding seal. It is known for the sliding seal to have a multi-part metal valve which opens when the seal reaches the end of its travel. This action allows the buffer fluid through the sliding seal to reach the sample fluid. This action allows buffer fluid to carry on pushing the sample fluid toward the chromatography column with minimal mixing and also allows the buffer fluid to attempt to clean the sample holder. However, the known valve is complicated, and consequently expensive. In addition, the large number of parts makes the valve difficult to clean.

An embodiment of the present invention addresses, the shortcomings mentioned above, as well as other problems with prior designs.

According to a first aspect of the invention, there is provided a fluid sample holder suitable for allowing a fluid sample to be delivered to, or received from, fluid processing equipment, the sample holder comprising: a sample fluid reservoir; a sample fluid port for providing fluid communication between said sample fluid reservoir and fluid processing equipment; a buffer fluid port also for providing fluid communication between the reservoir and said fluid processing equipment; and a sliding seal within the reservoir having an external area which substantially sealingly engages with a wall of the reservoir thereby defining a first and a second fluid separated regions in the reservoir, said first region being in fluid communication with the sample fluid port, and said second region being in fluid communication with the buffer fluid port, the sliding seal being displaceable within the reservoir by means of a working fluid pressure differential between the first and second regions to thereby change the respective volumes of the first and second regions, and at least the external area being formed from material which elastically flexes when subjected to a pressure differential greater than the working fluid pressure differential and when so flexed allows fluid flow between the first and second regions.

In an embodiment, the sliding seal has an outer shape which includes a generally cylindrical surface with a narrowed mid portion to form an hourglass shape, and optionally said external area of the sliding seal is at or adjacent one end of the cylindrical surface.

Preferably, the outer shape of the sliding seal further includes a plurality of recesses, each recess being open to the second region for allowing fluid communication between the narrowed mid portion and the second region.

More preferably, the recesses each include inner surfaces which are oblique to a plane parallel to the general centre line of the cylindrical outer surface.

In an embodiment, the sliding seal is hollow and the hollow is open to the first region.

Preferably, the walls of the sliding seal between the hollow and the outer shape of the sliding seal are sufficiently thin to allow said flexing.

In an embodiment, said flexing occurs at the sealing area adjacent the plurality of recesses.

In an embodiment, the sliding seal, including the external area is formed from a single piece of material, optionally a single piece of moulded material, optionally a single piece of moulded plastics material.

According to a second aspect of the invention there is provided a sliding seal for fluid separation of two regions of a fluid reservoir, the sliding seal being displaceable within the reservoir by means of a working fluid pressure differential between said two regions to thereby change the respective volumes of the two regions substantially without fluid flow past the seal, the seal comprising an external area for slidingly sealingly engaging with a wall of the reservoir, the seal being formed from a single piece of moulded plastics material which elastically flexes when subjected to a pressure differential greater than said working fluid pressure differential and when so flexed allows fluid flow between the two regions.

According to third aspect of the invention there is provided fluid processing equipment, including a sample holder or a sliding seal according to the first or second aspects.

According to fourth aspect of the invention there is provided a chromatography column, including a sample holder or a sliding seal according to the first or second aspects.

According to fifth aspect of the invention there is provided a method for delivering fluids to a chromatography column apparatus, including the steps of:

providing a sample fluid holder containing a sample fluid;

operating said apparatus to cause a buffer fluid to flow under a working pressure into said sample holder;

causing a sliding seal within the sample holder to be displaced by said buffer fluid thereby causing only said sample fluid in the sample holder to exit the sample holder through a sample fluid port;

allowing said displacement of said sliding seal to reach an end point thereat said working pressure is caused to increase; and causing the buffer fluid to flow past the sliding seal under the influence of said increased working pressure, by means of elastic flexing of an external area of the sliding seal.

The invention extends to any feature described herein, for example, a sample holder or fluid processing equipment substantially as described herein, optionally with reference to the drawings.

The invention can be put into effect in numerous ways, one embodiment only being described below, with reference to the accompanying drawings, wherein.

Figure 1:
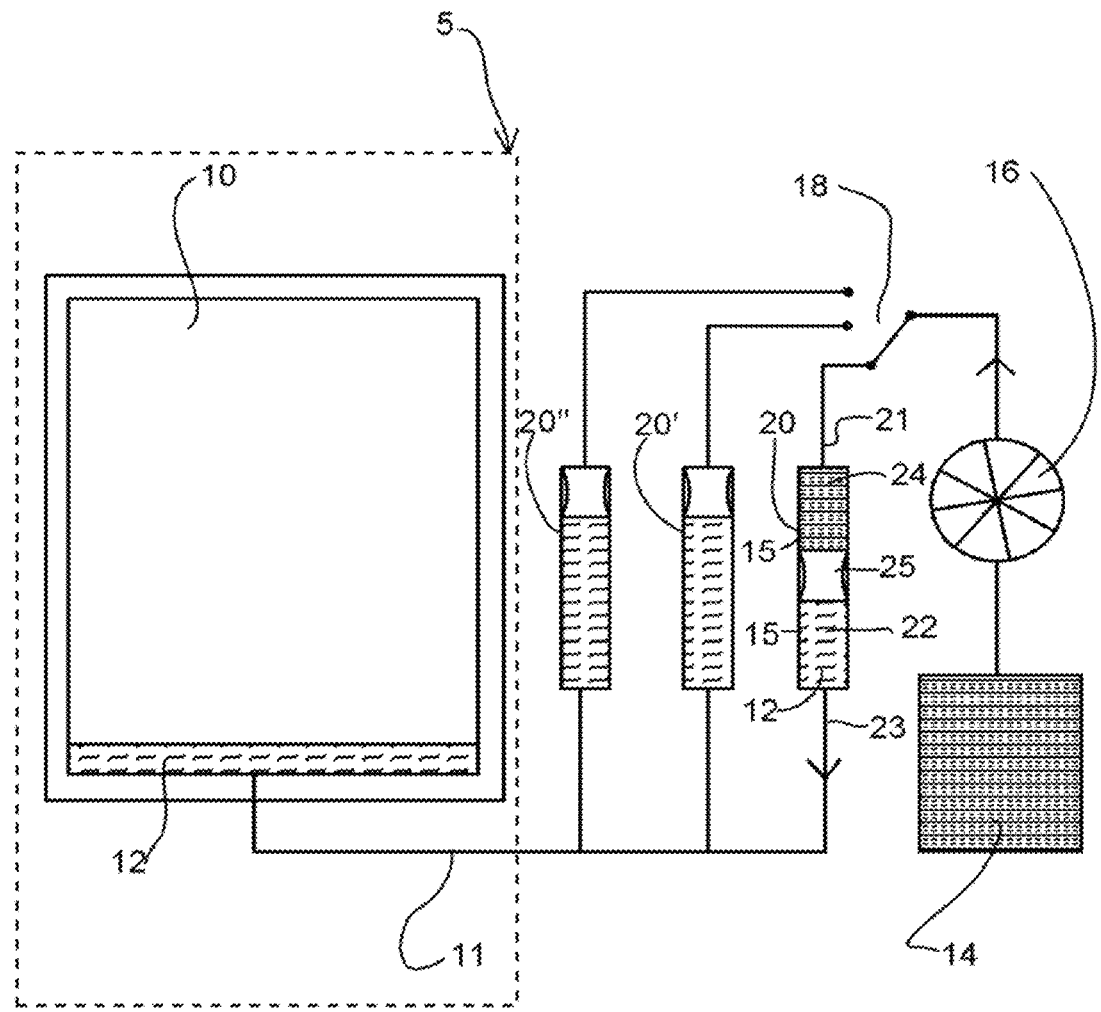
FIG. 1 shows a general arrangement of a sample holder in use with fluid processing equipment.

Referring to FIG. 1 there is shown schematically fluid processing equipment 5 in the form of a chromatographic column 10, having a supply conduit 11, fed, in this case, by a plurality of fluid sample holders 20, 20' and 20". Each sample holder is the same but sample holder 20 is described in more detail below. The sample holder 20 has a fluid reservoir 15 including an internal first region 22 and second region 24 separated by a sliding seal 25. The first region 22 retains a sample fluid, whereas a second region 24 receives a buffer fluid 14. The sample holder 20 is selectively connected to a pump 16, via a selection valve 18, and is able to receive buffer fluid under pressure via a buffer fluid port 21. The sliding seal 25 moves under the influence of the pressurised buffer fluid 14 and causes the sample fluid 12 in the first region 22 to flow out of the holder 20 through a sample fluid port 23. The sample fluid 12 then flows along the conduit 11 into the chromatography column 10 where it is employed. For example, the sample could be used in a process for the purification of proteins.

To this point the described features are generally conventional. However, the construction of the sample holder 20 has been improved, and these improvements are described below.

Figure 2:
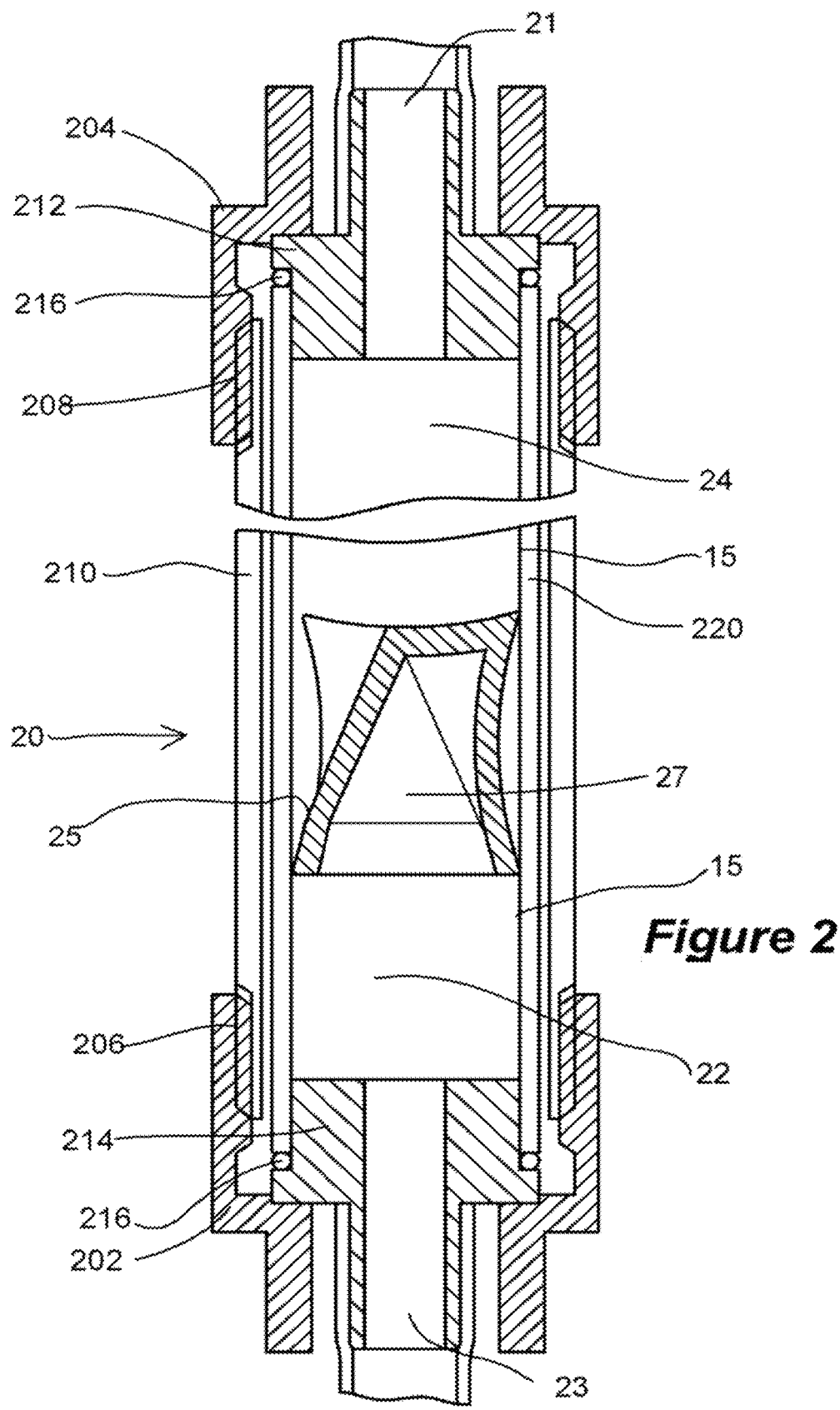
FIG. 2 shows a section through a sample holder of the type shown generally in FIG. 1.

With additional reference to FIG. 2, the sample holder 20 has two end fittings 202 and 204 which each include an integral threaded portion 206 and 208 respectively. The threaded portions 206 and 208 each fit with an outer tube 210 having complementary threaded ends. The two end fittings are rotated to clamp pipe connectors 212 and 214 to each end of an inner tube 220. A sealing ring 216 between each pipe connector and the inner tube 220 provides a fluid tight seal.

The ports 21 and 23 are formed by apertures in the pipe connectors 214 and 212. Thus, a sealed holder 20 is provided which has two ports for fluid communication with fluid processing equipment described above. Both the inner and outer tubes may be formed from transparent material, and it is preferred that the inner tube 220 is formed from glass material to provide a relatively inert sample wall surface and the outer tube is formed from a transparent or translucent plastics material to catch any shattered glass should the inner tube break under pressure. The inner tube 220 forms the sample fluid reservoir 15.

The sliding seal 25 is constructed from moulded material, for example a one piece moulded plastics, such as a polyetheretherketone (PEEK), a polypropylene (PP) or a high density polypropylene (HDPP). The seal 25 is generally cup shaped with its hollow 27 facing downwardly, and is shown in section in FIG. 2. It will be apparent from FIG. 2 that the moulded seal 25 has a relatively thin wall section and so it can elastically flex or deform under fluid pressure.

Figure 3:
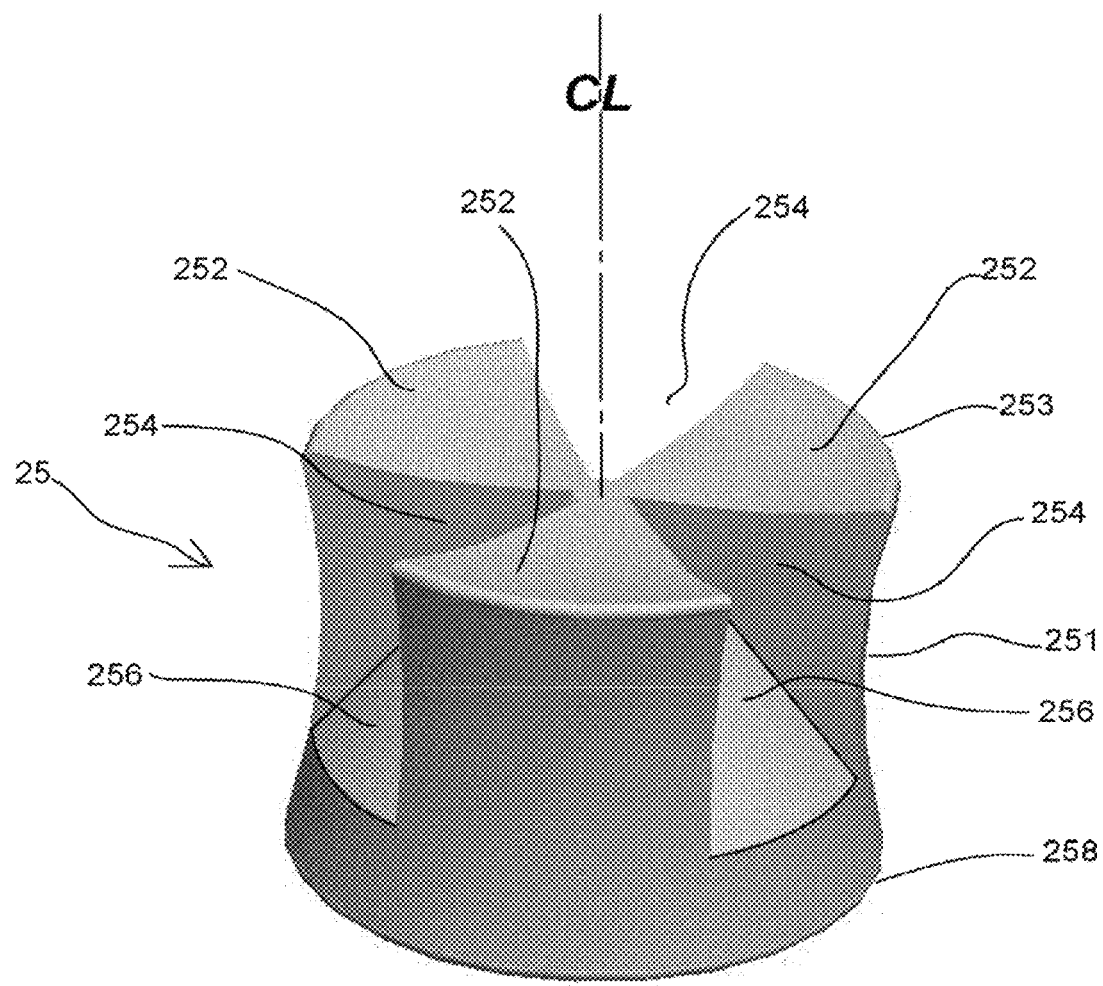
FIGS. 3 and 4 show pictorial views of a sliding seal used in the sample holder of FIG. 2.
Figure 4:
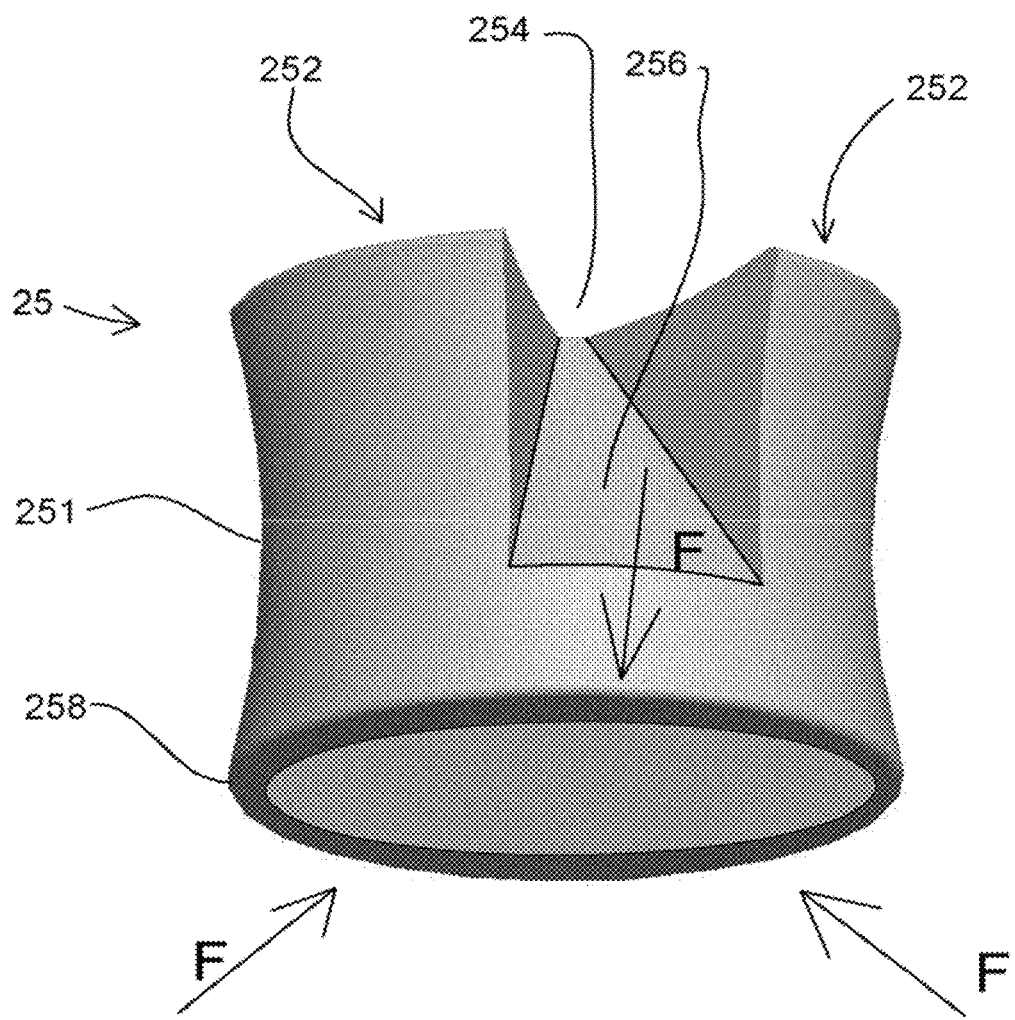

FIGS. 3 and 4 show the seal 25 in more detail. The seal 25 has a generally 'hour glass' shape, that is, it is cylindrical with a diameter which is narrower at its middle 251 than at its top 253 and bottom 258 diameters. The seal includes a generally 'clover leaf' end face which has three equi-spaced supporting end faces 252, and three recesses 254. Each recess includes an inner face 256 which is oblique to a centre line CL of the seal 25.

When fitted in the inner tube 220, a sliding sealing area is provided by the lower diameter 258. Fluid pressure in the region 24 acts on the end faces 252 and the inner faces 256 to force the seal downwards. When the seal reaches its lowermost position and abuts the lower pipe connector 214, then a backpressure will build in the region 24 and around the mid diameter 251. This back pressure is relieved by deformation of the seal 25. In more detail, the seal 25 will flex or deform elastically by being compressed so that fluid will pass between the sealing area 258 and the inner tube 220. The oblique faces 256 will be forced toward the centre line CL and in so doing will push the sealing area 258 in the directions of arrows F, that is, into a three lobed shape.

A working pressure differential between the first and second regions of around 0.01 to 0.08 MPa is envisaged with negligible leakage past the seal area 258 and to provide downward movement of the sliding seal 25 to cause a net fluid flow out through the port 23. Flow past the seal area 258 occurs when the working pressure differential is exceeded and it is intended that a pressure differential exceeding around 0.08 to 0.1 MPa will cause that flow around the seal 25. This pressure differential will occur when the seal 25 reaches it lowermost point when it can slide no more.

It will be apparent to the skilled addressee that additions, omissions or modifications to the foregoing description are possible within the ambit of the invention defined herein.

For example, the use of the terms such as 'up', 'upper', or 'upward' etc. and 'down', 'downward', 'lower' or 'lowermost' etc. are used to describe the arrangement illustrated, and are not intended to limit possible alternative orientations. The term 'fluid' is used to include liquids and other fluent material, including but not limited to gases and fluent particulate or gel-like materials. The invention is primarily intended to introduce fluids into the equipment described above, but could also be used to collect samples from fluid processing equipment by reversing the pressure differential so the that seal 25 moves upwardly.

The sliding seal 25 is described as being hollow, although it need not be so where the material of the seal is sufficiently elastically flexible that it can flex to allow fluid flow under pressure which exceeds the normal working pressure.

The holder described is particularly suitable for automated equipment where the sample holder needs to be substantially completely emptied and either flow needs to continue to push sample fluid into the equipment or the holder needs to be thoroughly flushed with buffer fluid, for example, prior to being disconnected from the equipment. However, the continuation of flow, or the flushing steps need not always be employed.

The embodiment described and illustrated thus provides a simple and inexpensive sliding seal which is easy to clean and reuse. The sliding seal itself may be employed in other applications, for example where a sliding seal is displaceable within the reservoir by means of a working fluid pressure differential between first and second regions of the reservoir to thereby change the respective volumes of the first and second regions substantially without fluid flow past said seal, and where the seal has an external area for slidingly sealingly engaging with a wall of the reservoir, the seal being formed from a single piece of moulded plastics material which elastically flexes when subjected to a pressure differential greater than the working fluid pressure differential and when so flexed allows fluid flow between the first and second regions.

What is claimed is:

1. A fluid sample holder suitable for allowing a fluid sample to be delivered to, or received from, fluid processing equipment, the sample holder comprising:
   a sample fluid reservoir;
   a sample fluid port for selectively providing fluid communication between the sample fluid reservoir and the fluid processing equipment;
   a buffer fluid port for selectively providing fluid communication between the reservoir and the fluid processing equipment; and
   a sliding seal positioned within the reservoir, the sliding seal having an external area that substantially engages with a wall of the reservoir thereby defining a first region substantially sealed and separated from a second region within the reservoir, the first region being in fluid communication with the sample fluid port, and the second region being in selective fluid communication with the buffer fluid port, wherein the sliding seal is displaceable within the reservoir using a working fluid pressure differential between the first and second regions to thereby change the respective volumes of the first and second regions, and wherein at least a portion of the external area is formed from material that elastically flexes when subjected to a pressure differential greater than the working fluid pressure differential and when so flexed allows fluid flow between the first and second regions.

2. The fluid sample holder of claim 1, wherein the sliding seal has an outer shape which includes a generally cylindrical surface with a mid portion diameter smaller than a top diameter and a bottom diameter, and the external area of the sliding seal is at or adjacent one end of the cylindrical surface.

3. The fluid sample holder of claim 2, wherein the outer shape of the sliding seal further includes a plurality of recesses, each recess being open to the second region allowing fluid communication between the mid portion diameter and the second region.

4. The fluid sample holder of claim 3, wherein the recesses each include inner surfaces positioned oblique to a plane parallel to the center line of the cylindrical outer surface.

5. The fluid sample holder of claim 4, wherein the sliding seal is comprises a hollow opening toward the first region.

6. The fluid sample holder of claim 5, wherein the walls of the sliding seal between the hollow and the outer shape of the sliding seal are sufficiently thin to allow flexing of the external area.

7. The fluid sample holder of claim 6, wherein flexing of the external area occurs at the sealing area adjacent the plurality of recesses.

8. The fluid sample holder of claim 1, wherein the sliding seal is formed from a single piece of material.

9. The fluid sample holder of claim 8, wherein the single piece of material is molded.

10. The fluid sample holder of claim 9, wherein the molded material comprises, at least in part, a plastic.

11. The fluid sample holder of claim 1, wherein the fluid processing equipment is a chromatography column.

\* \* \* \* \*